(12) United States Patent
Binggeli et al.

(10) Patent No.: US 8,580,324 B2
(45) Date of Patent: Nov. 12, 2013

(54) FERMENTATION PROCESS

(75) Inventors: Eva Christina Maria Binggeli, Männedorf (CH); Thomas Muench, Illnau (CH)

(73) Assignee: Givaudan SA, Vernier (CH)

( * ) Notice: Subject to any disclaimer, the term of this patent is extended or adjusted under 35 U.S.C. 154(b) by 87 days.

(21) Appl. No.: 13/132,978

(22) PCT Filed: Dec. 11, 2009

(86) PCT No.: PCT/CH2009/000393
§ 371 (c)(1),
(2), (4) Date: Jun. 6, 2011

(87) PCT Pub. No.: WO2010/066061
PCT Pub. Date: Jun. 17, 2010

(65) Prior Publication Data
US 2011/0262593 A1    Oct. 27, 2011

Related U.S. Application Data

(60) Provisional application No. 61/122,028, filed on Dec. 12, 2008.

(51) Int. Cl.
*A23L 1/221* (2006.01)
(52) U.S. Cl.
USPC .......................................... 426/44; 426/650

(58) Field of Classification Search
USPC .................................. 426/44, 650; 435/252.5
See application file for complete search history.

(56) References Cited

U.S. PATENT DOCUMENTS

| 3,663,238 A | 5/1972 | Karas et al. |
| 5,705,205 A | 1/1998 | Brunerie |

FOREIGN PATENT DOCUMENTS

| JP | 58 043757 A | 3/1983 |
| KR | 100 255 037 B1 | 7/2000 |
| WO | 2004 091316 A1 | 10/2004 |

OTHER PUBLICATIONS

Rollng, W. F. M. et al. 2001. Microogranisms with a taste for vanilla: Microbial ecology of Traditional Indonesian Vanilla curing. Appl. Environ. Microbiol. 67: 1995-2003.*
Biocatalysts—Technical Bulletin No. 110. 2005. The Use of enzymes in vanilla exatraction.*

\* cited by examiner

*Primary Examiner* — D Lawrence Tarazano
*Assistant Examiner* — Hamid R Badr
(74) *Attorney, Agent, or Firm* — Norris McLaughlin & Marcus PA

(57) ABSTRACT

Provided is a fermentation process wherein green ripe uncured vanilla beans are incubated with *bacillus subtilis* in isolated form to convert glucovanillin to vanillin while consistently forming a fully developed well-balanced vanilla aroma without off-notes.

13 Claims, No Drawings

FERMENTATION PROCESS

This is an application filed under 35 USC 371 of PCT/CH2009/000393.

TECHNICAL FIELD

Disclosed is a fermentation process employing *Bacillus subtilis* wherein green (ripe but uncured) vanilla beans are incubated with *B. subtilis* to convert glucovanillin to vanillin, and to convert other precursor vanilla flavor compounds bound to glucose to the relevant non-glucose-bound vanilla flavor compound.

BACKGROUND

Vanilla extracts comprising vanillin and other vanilla flavor compounds are produced by subjecting ripe green vanilla beans to a curing and extraction process. The curing process releases vanillin from glucovanillin and forms the brown-black whole vanilla beans commercially available. The cured beans can then be extracted to form a liquid vanilla extract.

The curing period usually lasts many weeks or months, involves repeated quality controls and depends on the environmental conditions. While the sensory profile/flavor of the resulting extracts can be excellent, even under optimal conditions the vanillin yield is very low and usually up to about 2.2% per dry weight of vanilla beans. Shorter curing and extraction processes known in the art either result in a similarly low average vanillin yield, and/or the sensory profile is not fully developed/less complex with an unbalanced flavor profile, and/or contains off-notes. One example of such a process is in U.S. Pat. No. 3,663,238, which describes a curing/drying process for green vanilla beans in a sweating tank that involves cutting green beans and incubating them at 140° F. (60° C.) for 70-78 hours and drying them with forced air at the same temperature to a moisture content of 35-40%, and at room temperature to a final moisture content of 20-25%.

The long curing period of traditional processes employs naturally occurring enzymatic reactions. The enzymatic reactions in the vanilla beans from its precursor glucovanillin to vanillin are believed to be mainly caused by residual plant enzymes, in particular glucosidase enzymes.

Notably, *B. subtilis* was not previously known to be involved in or useful for the production of vanilla flavour compounds in vanilla beans. The bacterium was known merely for being capable of expressing various enzymes, including, among many others, the b-glucosidase enzyme.

SUMMARY

Provided is a fermentation process to produce vanilla flavor compounds, wherein green ripe uncured vanilla beans are incubated with *B. subtilis* from a stock culture or with pre-cultured *B. subtilis*.

The use of *B. subtilis* in a process to produce vanillin from glucovanillin and to convert other precursor vanilla flavor compounds bound to glucose to the relevant non-glucose-bound vanilla flavor compound (including, without limitation, vanillic acid, p-hydroxybenzaldehyde, and p-hydroxybenzoic acid) as described herein produces a comparable or higher yield than traditional processes but with a more consistent fully developed complex sensory profile and without off-notes. Off-notes often present in traditional processes, without wishing to be bound by theory, appear to be caused at least in part by various bacteria and fungi that are present on or in the vanilla beans. The addition of *B. subtilis* reduces or avoid these off-notes. The effect can be even more improved by reducing the microorganism count prior to the addition of *B. subtilis*.

Provided is the following:

(1) A process of fermenting vanilla beans comprising the incubation of uncured vanilla beans with *Bacillus subtilis* in isolated form, wherein the incubation with *B. subtilis* lasts for about 24 hours to about 120 hours. For example, without limitation, *B. subtilis* can be added to the vanilla beans from a stock culture of *B. subtilis*, or as a pre-culture of *B. subtilis*.

(2) The process as described herein, including under (1), wherein the incubation with *B. subtilis* is performed at a temperature from about 40° C. to about 65° C.

(3) The process as described herein, including under any one of (1) and (2), wherein the uncured vanilla beans are dried and reconstituted with water previous to the incubation with *B. subtilis*.

(4) The process as described herein, including under any one of (1) to (3), wherein before incubation with *B. subtilis*, the uncured vanilla beans are washed.

(5) The process as described herein, including under any one of (1) to (4), wherein after the incubation with *B. subtilis*, one or more enzymes comprising a beta-glucosidase enzyme are added.

(6) The process as described herein, including under any one of (1) to (5), wherein after the incubation with *B. subtilis*, the vanilla beans are dried to a low moisture of about 30% to 20% at temperature from about 20° C. to about 60° C.

(7) The process as described herein, including under any one of (1) to (6), wherein a solvent is added to the resulting product to form a vanilla extract.

(8) The process as described herein, including under any one of (1) to (7), wherein the incubation with *B. subtilis* is performed in a vessel selected from the group consisting of a sweating tank wherein the vanilla beans are stationary, and a stirred tank.

(9) The process as described herein, including under (8), wherein the incubation with *B. subtilis* is performed in a closed system of a sweating tank wherein the vanilla beans are stationary and wherein the exudate from the vanilla beans is being recycled.

(10) The process as described herein, including under any one of (1) to (8), wherein the incubation with *B. subtilis* is performed in an open system.

(11) The process as described herein, including under any one of (1) to (10), wherein *B. subtilis* is selected from the group consisting of *B. subtilis subtilis*, a wildtype *B. subtilis* strain isolated from vanilla beans, and *B. subtilis subtilis* strain NRRL B-50118.

(12) A fermented vanilla bean product wherein in its fermentation *B. subtilis* was provided in isolated form.

(13) The fermented vanilla bean product as described herein, including under (13), wherein *B. subtilis* was provided from a stock culture or as a pre-culture.

(14) The fermented vanilla bean product as described herein, including under (12), selected from the group consisting of vanilla pods, partially comminuted vanilla pods, comminuted vanilla pods, ground vanilla pod powder, vanilla extract.

(15) The *B. subtilis subtilis* strain NRRL B-50118.

DETAILED DESCRIPTION

Applicant discovered that incubation with *B. subtilis* can be used to ensure a good vanillin yield and provide a consistently high quality well-balanced complex vanilla flavor profile without off-notes in the resulting vanilla beans and their extracts. Without wishing to be bound by theory, applicant believes that this is due to the microbial enzymes converting glucovanillin to vanillin (and other gluco-precursor vanilla flavor compounds bound to glucose to the relevant non-glucose-bound vanilla flavor compound) to a significant extent, instead of, or in addition to, the plant enzymes. Again, without wishing to be bound by theory, the potential antimicrobial, antiviral and antifungal properties of *B. subtilis* on the variety of microorganisms naturally occurring on or in vanilla beans may contribute to reduce or avoid the formation of off-notes during fermentation. Alternatively or additionally, the growth of *B. subtilis* may be so fast in comparison to other naturally present microorganisms that it deprives them of their necessary substrate. Furthermore, *B. subtilis* is a very adaptable hardy microorganism that requires little and will thrive in many minimal media under almost all conditions, including aerob and anaerob conditions.

Vanilla beans are incubated with *B. subtilis* under conditions that allow for bacterial growth until the desired degree of degradation of glucovanillin to vanillin and other vanilla flavor compounds from their gluco-precursors is achieved. To form an extract, a solvent may be added. The process is described in detail below.

There are currently three major cultivars of the genus vanilla grown globally, all derived from a species originally found in Mesoamerica: *Vanilla planifolia* (*V. planifolia*, syn. *V. fragrans*), grown on Madagascar, Réunion and other tropical areas along the Indian Ocean; *V. tahitensis*, grown in the South Pacific; and *V. pompona*, found in the West Indies, Central and South America. The majority of the world's vanilla that is produced is the *V. planifolia* variety, grown in a small region of the east African nation of Madagascar and Indonesia, and which when produced in Madagascar is more commonly known as "Madagascar-Bourbon" vanilla.

Vanilla spec. include, without limitation, *V. planifolia, V. tahitensis, V. pompona*, and hybrids of these or other vanilla spec. plants, for example, without limitation, hybrids of *V. planifolia* and *V. pompona*.

Vanilla beans require about 6 to 9 months to fully develop on the vine, during which stage the beans are green in color. At the end of the growing stage the beans are still green with a small yellow tip and sometimes referred to as "blossom-end yellow" or "mature", which is the stage at which ripe green beans are harvested. When traditionally cured, they turn from green to brown. A green vanilla bean therefore is a mature uncured bean.

The vanilla beans incubated with *B. subtilis* are uncured beans, i.e. beans that have not yet been subjected to a process to release vanillin from glucovanillin. The uncured beans may be fresh green beans, or "green" (uncured) beans that have been dried and then reconstituted with water (which are brown in color). The latter usually provide a lower vanillin yield when compared to green beans that have not been dried and reconstituted. The vanilla beans may be used as whole beans, or in comminuted or ground form. The vanilla beans may be comminuted by any suitable means to render them to pieces, for example, without limitation, about 1-2 cm long. Any suitable tool or mechanism may be employed. For example, the beans may be cut or chopped. The cuts generally proceed transversely of the long axes of the beans though other directions are possible as well.

Optionally, the beans are washed prior to incubation with *B. subtilis* (thereby reducing the initial microbial count and reducing unwanted microbes) that may naturally occur on the beans. The washing of beans may be performed in water, in water and detergent, or in an aqueous alcohol solution, and at a high enough temperature for a long enough time to reduce the microbial count. For example, washing may be performed in water and detergent at ambient temperature (about 20-30° C.), or in hot water (about 60-85° C., depending on length of exposure, for example, about 1 min at about 85° C., or about 5 min at about 60° C.), or in 70% alcohol for about 5 to 10 min.

For microbial incubation of the vanilla beans, *Bacillus subtilis* (*B. subtilis*) is used. *B. subtilis* is a very well known and well characterized gram positive bacterium commonly found in soil. It usually grows aerobic, but can grow anaerobically as well. *B. subtilis* provides a very good vanillin yield that other *Bacillus* bacteria appear not to be able to achieve. An example of a very suitable *B. subtilis* subspecies is *B. subtilis subtilis*, and *B. subtilis* strain NRRL B-50118, deposited Mar. 20, 2008 with the ARS Patent Culture Collection.

Other *B. subtilis subtilis* or *B. subtilis* strains, in particular, for regulatory reasons, wild type strains isolated from vanilla beans, may be used. Primary isolations of wildtype strains can be performed as is well known in the art, for example on nutrient agar (peptone 5 g/l, beef extract 3 g/l, agar 15 g/l, pH6.8) or plates of J-agar (tryptone 5 g/l, yeast extract 15 g/l, K2HPO4 3 g/l, glucose 2 g/l, agar 20 g/l, pH 7.4).

Various suitable growth media suitable for *B. subtilis* are well known in the art. *B. subtilis* has little requirements for its growth conditions and media, it grows in a minimal defined medium with no added growth factors. A. Demain (J. Bacteriol. 1958 May; 75 (5): 517-522) describes some examples of constituents suitable minimal media should include. Minimal media are particularly useful to isolate wildtype strains. For culture, usually nutrient media are used. Nutrient media contain a carbon source (for example, without limitation, glucose), water, various salts, and a source of aminoacids/nitrogen. Nutrient agar and nutrient broth (for example, comprising as aminoacid/nitrogen source peptone and meat extract, at a neutral pH of about 7) are suitable to culture *B. subtilis*, for example, LB medium is a suitable standard medium. A standard culture temperature is about 30° C. to about 37° C.

For a *B. subtilis* pre-culture, any suitable standard medium may be used.

*B. subtilis* may be cultured according to well known culture conditions at a suitable temperature, pH and moisture content. Suitable conditions include, without limitation, about 25° C. to about 60° C., with a temperature optimum at about 37° C., a pH of about 4.5 to about 7.5, for example, without limitation, pH 5.5 to 6.5, a moisture content of 55% or higher, and optionally a medium to adjust osmotic pressure. When incubated with the vanilla beans, the same conditions apply except for a higher culture temperature from about 45° C. to about 65° C., for example, without limitation, from about 45° to about 60° C., or from about 50° C. to about 60° C.

Optionally, oxygen may be added/sufficient aeration may be provided, for example, without limitation, by a fan, to reduce growth of unwanted anaerobic bacteria.

Incubation of the vanilla beans with *B. subtilis* can be done in any suitable environment or vessel, for example, without limitation, in a tank or sweating tank, for example as described in U.S. Pat. No. 3,663,238, The exudate ("sweat") of the vanilla beans, for example in a sweating tank, may optionally be recycled; alternatively, an open system may be used.

The container may optionally be stirred to provide mixing and/or aeration.

For example, in U.S. Pat. No. 3,663,238, a stainless steel vessel is equipped with stacked perforated trays and provided a temperature control and a closed exudate recirculation system. The exudate ("sweat" of the heated beans) is collected and may contain bacteria derived from the surface of the beans. The exudate flows through the perforations/holes in the trays through all stacked trays to an outlet at the bottom of the vessel, and is collected and reintroduced to the beans from the top of the vessel to avoid drying out and to avoid loss of microorganisms. The beans are placed into the vessel in a number of mono-layers on the perforated trays to allow air for the bacteria. Exudate collection and/or reintroduction is optional and depends on the degree of exudate development.

Alternatively, the incubation of the vanilla beans with *B. subtilis* can be performed in closed or vented bags, for example, without limitation, plastic bags, or in a box, room or other contained environment (for example on shelves), or even in an open system, for example, outside exposed to ambient air, provided the moisture content of the air is appropriately high (about 55% humidity or higher).

The incubation temperature is from about 40° C. to about 65° C., for example, without limitation, from about 45° to about 60° C., or from about 50° C. to about 60° C.

Depending on the container used for incubation, and depending on whether stirring is used, there may be a temperature gradient in the container and care should be taken to ensure not only a suitable average temperature but also that the maximum temperature is not significantly exceeded for too long, in order to avoid sporulation and ensure sufficient growth or at least survival rates of *B. subtilis*.

The duration of incubation of the vanilla beans with *B. subtilis* will depend on various parameters including temperature, pH, etc., and whether a pre-culture is used or *B. subtilis* is directly added from a stock culture (the latter requires more time). Incubation should be stopped once the optimal vanillin and vanilla flavour compound yield is reached. The incubation time should be about 24 hours to about 120 hours. Usually 2 to 4 days are sufficient. Longer incubation, especially at the higher temperatures, will start to degrade vanillin and other vanilla flavour compounds, longer incubation especially at the lower end of the temperature range and especially when the beans are stationary will promote the growth of molds and other undesirable microorganisms that can spoil the product and cause off-notes. Shorter incubation will not allow a complete degradation of glucosides (glucovanillin and other glucose-bound vanilla flavor compounds) and the product will not have a fully developed well-balanced flavor profile.

After *B. subtilis* incubation, the vanilla beans may be dried, or a vanilla extract may be directly formed.

Optional Drying Prior to Extraction:
Any suitable method may be used to dry the beans to a low moisture content of about 30% to about 20% at temperature from about 20° C. up to about 60° C. Suitable methods include, without limitation, vented drying out in the sun or in a well vented room, and drying in a vented oven.
To further develop the non-vanillin/non-glucose-precursor vanilla flavour compounds part of the aroma including the part due to Maillard reactions, slow drying will usually give better results. A suitable drying schedule is to dry 2-5 days to about 30% moisture, then for 3 to 9 months to about 20 to about 25% moisture (storage in vented sacks in a well vented room for the latter step).

To form a vanilla extract, a solvent may be added to the incubation container, for example, without limitation, a tank, to form a vanilla extract. Suitable containers include, without limitation, a conical extractor/stirred tank, and a box extractor wherein the beans are stationary.

After extraction, the resulting extract can be concentrated or diluted as desired. The extraction temperature should not exceed a maximum of about 45° C. to avoid any partial degradation of vanillin or other vanilla flavor compounds.

A vanilla extract consists substantially of extractive matter of vanilla beans from vanilla plants and optionally a solvent. For example, certain sugars may be added in some countries. Solvents include, without limitation, alcohol/ethanol, and water. Solvents that are not food-grade have to be removed or sufficiently reduced in concentration to form the end product sold to the consumer according to nationally differing regulatory requirements.

Optionally, food-grade solvent may be added to adjust the concentration or so-called fold of the vanilla extract end product as desired.

Any solvent able to bring vanillin and/or additional vanilla flavors into solution can be used. Useful solvents include water and alcohols, including without limitation organic alcohols. Organic alcohols include, without limitation, alkanols having up to 4 carbon atoms, for example, ethanol, isopropanol, propanol, low molecular weight glycols and polyols including, without limitation, propylene glycol, butylene glycol, or glycerin, or mixtures thereof.

Suitable solvents include, without limitation, aqueous alcohol solvents containing at least one alcohol miscible with water in the proportions employed. Suitable aqueous alcohol solvent includes, without limitation, mixtures of ethanol and water, for example, ethanol/water (50:50).

If a food-grade solvent is used it does not need to be removed afterwards, which is more efficient particularly in the final process steps. Food-grade solvents include, without limitation, ethanol, water, mixtures of ethanol and water, ethanol/water (50:50), and mixtures thereof. Another alternative may be supercritical fluid extraction.

Solvents that are not food-grade, or not food-grade in all legislations or in all concentrations for all end products, for example, without limitation, hexane, ethylmethylketone, methyl acetate, dichloromethane, fusel oil, or mixtures thereof, have to be either completely removed or at least partially removed (to a specific low concentration that usually varies according to the national food regulations) to form the end product sold to the consumer. The term "fusel oil" designates a distilled concentrated liquid obtained in small amounts as a by-product of alcoholic fermentation and distillation that consists of a mixture chiefly of alcohols, such as isopentyl alcohol, amyl alcohol, isobutyl alcohol, isopropyl alcohol and propyl alcohol.

Optionally, the resulting vanilla extract can be concentrated by at least partly removing the solvent.

Optionally, any residual glucovanillin (and other precursor vanilla flavor compounds bound to glucose) in the resulting product or extract may be converted to vanillin (or the relevant non-glucose-bound vanilla flavor compound) by adding beta-glucosidase (commercially available from various sources including Biocatalysts Limited, Cardiff, UK) or a mixture containing a beta-glucosidase enzyme and optionally additional enzymes. The amount of beta-glucosidase enzyme depends on the incubation parameters including duration, temperature, amount and concentration of substrate and of solvent.

Too much enzyme will not have an additional benefit and may introduce off-tastes.

If a mixture of enzymes containing 5 units per g of beta-glucosidase is used, then an amount of enzyme 0.005 to 0.2 times the vanilla bean charge weight is usually sufficient, for example, without limitation, 0.02 to 0.1, or 0.035 to 0.15 times.

A suitable solvent to use in the enzyme incubation includes water and mixtures of water with another solvent compatible with the enzyme. For example, ethanol should be less than 25% for optimal enzymatic reaction.

The enzyme is incubated within a suitable temperature range, for example, 20° C. to 80° C. or 40° C. to 60° C., for example, without limitation, near its temperature optimum at about 55° C. to 60° C., and held at this temperature for a sufficient time to convert glucovanillin to the desired vanillin yield. Continuous stirring will ensure a constant temperature and concentrations. Smaller volumes may not require stirring.

The incubation time will depend on the amount and concentration of the enzyme and substrate, solvent present, temperature chosen, for example, without limitation, 1 hour to 2 days or longer. Usually, 24 hours are sufficient.

Preferably, the mixture should be stirred during the enzymatic reaction to ensure sufficient mixing, constant temperature throughout the reaction vessel, and access of enzyme to substrate.

After the enzymatic incubation, optionally, the vanilla extract may be concentrated and/or a food-grade solvent may be added as described above.

The vanilla beans and their extracts described herein provide a fully developed and well-balanced flavor profile comprising the major vanilla flavor compounds. Major vanilla flavor compounds include, without limitation, phenolic compounds, furan compounds, fatty acid compounds, compounds formed by reaction with ethanol, and acetaldehyde diethyl acetal.

Phenolic vanilla flavor compounds include, without limitation, acetovanillone alpha-ethoxy-p-cresol, benzoic acid, guaiacol, 4-methylguaiacol, p-hydroxybenzaldehyde, methylparaben, methyl vanillate, 2-methoxy-4-vinylphenol 5-methoxyvanillin, phenol, Vanillin, vanillic acid, vanillyl alcohol, vanillyl ethyl ether, and p-vinylphenol.

These phenolic vanilla flavor compounds, in particular guaiacol, should be present in a low concentration so that they do not dominate, resulting in an unbalanced flavor.

Furan vanilla flavor compounds include, without limitation, 2-furfural, 2-furfurol 5-(hydroxymethyl)-2-furfural, 5-methyl-2-furfural, 2-hydroxyfuraneol, gamma-butyrolactone (dihydro 2(3H)-furanone.

Fatty acid vanilla flavor compounds include, without limitation, linoleic acid, and palmitic acid.

Vanilla flavor compounds that are formed by the reaction with ethanol include, without limitation, etyl acetate, ethyl glycolyte, ethyl lactate, ethyl linoleate, ethyl pyrovate, ethyl levulinate, and diethylsuccinate.

EXAMPLES

Unless otherwise indicated, percentages are given as wt/wt and all ingredients and solvents are food grade. Vanilla beans were from *Vanilla planifolia* plants. Vanilla extracts below use the US "fold" unit, e.g. a single-fold vanilla extract is one which contains the extractive matter of one unit of vanilla beans (13.35 oz vanilla pods with a maximum moisture content of 25%) in one US gallon (35% alcohol) of product. Thus, a ten-fold vanilla extract is one which contains the extractive matter of ten units of vanilla beans per US gallon of finished product according to the FDA, Title 21.

Example 1a

Fermentation of Green Vanilla Beans with *Bacillus subtilis*

Reduction of Residual Microbes:
Green beans were exposed to hot water (about 85° C.) for about 1 to 4 min.

The green vanilla beans were fresh green vanilla bean with a percentage of moisture that is usually about 85% (wt/wt), or (see example 1b) dried green vanilla beans with moisture of less than 10% (as low as about 5%, which corresponds to completely dried beans—the residual 5% water cannot be removed by conventional sun or oven drying). The moisture percentage was determined using an infrared oven (Moisture Analyzer, Computrac, Model Max-1000, by Arizona Instruments) and weighing the beans before and after drying.

*B. subtilis subtilis* in 0.9% NaCl:
One tube of about 1 g of a lyophilized culture of a *B. subtilis subtilis* strain NRRL B-50118, isolated from vanilla beans and deposited Mar. 20, 2008 with the ARS Patent Culture Collection, was dissolved in 20 ml sterile nutrient broth (Bacto™ nutrient broth dehydrated for cultivation of non fastidious microorganisms, Difco, Laboratories Detroit, Mich., USA, 8 g/l of distilled water). The culture was incubated at 37° C. at 200 rpm for 2 to 3 days until spores developed (spores are determined optically with a microscope). 500 ml of nutrient broth was inoculated with the whole of this culture, the resulting culture again was incubated at 37° C. for further 2 to 3 days until spores developed. The cells were precipitated by centrifuge and the precipitate was redissolved in 5 liters of sterile 0.9% NaCl.

12 kg of green vanilla beans were cut in to 2 cm pieces and incubated for 1 hour at room temperature in 5 liters of *B. subtilis subtilis* in 0.9% NaCl prepared as described above. These *B. subtilis subtilis* exposed beans were filled into a curing tank vessel at 2 kg beans/layer (to give nearly a monolayer) and 6 layers deep on perforated metal plates. The curing tank vessel (also known as sweating tank) was a custom-made large-scale vessel as described by McCormick 1973 in U.S. Pat. No. 3,663,238. The *B. subtilis* exposed beans were cured at an average temperature of about 50° C. for 72 hours, with a maximum temperature of 60° C., no exudate was collected.

The curing tank vessel was emptied and the beans were left to dry slowly. The vanilla beans were dried with warm air at about 50° C. until 60% moisture was reached (for about 12 hours), then to 38% moisture at 40° C. (for about 5 h), and at ambient temperature of about 20 C until 30% moisture (for about 10-20 hours).

The resulting vanilla beans with moisture contents of 25 to 30% (wt/wt) were packed in plastic bags and stored at room temperature avoiding exposure to sunlight for about 3 months.

1.59 kg (or 3.5 lbs) of ground vanilla beans were extracted and concentrated to give 1 times the vanilla bean charge weight of the resulting extract. Vanilla beans were extracted five times with 50/50 (w/w) tap water and ethanol 2.27 kg or 5 lbs of solvent per extraction. Ethanol was added to adjust to about 40% (v/v) ethanol (about 0.3 times the vanilla bean charge weight) to achieve a final weight of the resulting 10 fold vanilla extract equal to 1 times the vanilla bean charge weight.

Example 1b

Fermentation of Dried Rehydrated Green Vanilla Beans with *Bacillus subtilis*

Preparation of Dried Green Vanilla Beans:
Green fully ripe vanilla beans with a high concentration (about 6% based on the dried weight of beans; usually green beans have about 16% dry substance, and after drying, about 90% dry substance) of glucovanillin determined by visual inspection (green bean with yellow tip) were used. Drying was performed by cutting the beans into pieces of about 2.5 cm length, and then incubating at about 85° C. (80° C. to 90° C.) in an oven until a moisture concentration of less than 10% was reached. The moisture percentage was determined using an infrared oven (Moisture Analyzer, Computrac, Model Max-1000, by Arizona Instruments) and weighing the beans before and after drying. The drying procedure takes from about 10 to 20 hours. Without wishing to be bound by theory, this may contribute to reduce microorganisms to an acceptable level so that the formed vanillin is not significantly degraded during fermentation.

0.400 kg of the dried and ground beans were re-moisturized with 2.0 liters of B. subtilis subtilis in 0.9% NaCl prepared as described in example 1a in a stirred tank.

The resulting mixture was stirred for 96 hours at 50° C. Ethanol was added to this mixture to form a single fold vanilla extract and mixed for 12 hours at 50° C. then cooled to 25° C. A single fold vanilla extract equal to 0.1 times the vanilla bean charge weight was prepared.

Example 2

B. subtilis Strain—16 S rRna based characterization, identification as B. subtilis subtilis B. subtilis subtilis strain NRRL B-50118, isolated from Vanilla planifolia vanilla beans cultivated in Madagascar and deposited Mar. 20, 2008 with the ARS Patent Culture Collection, was identified by 16S rRNA sequencing over 500 bp as follows.

The 16S rRNA gene was PCR amplified from genomic DNA isolated from pure bacterial colonies. Primers used for the amplification correspond to E. coli positions 005 and 531 (>500 bp package). Amplification products were purified from excess primers and dNTP's using Microcon 100 (Millipore) molecular weight cut-off membranes and checked for quality and quantity by running a portion of the products on an agarose gel.

Cycle sequencing of the 16S rRNA amplification products was carried out using AmpliTaq FS DNA polymerase and dRhodamin dye terminators. Excess dye-labeled terminators were removed from the sequencing reactions using a Sephadex G-50 spin column. The products were collected by centrifugation, dried under vacuum and frozen at −20° C. until ready to load. Samples were suspended in a solution of formamide/blue dextran/EDTA and denatured prior to loading. The samples were electrophoresed on an ABI Prism 377 DNA sequencer. Data was analyzed using Applied Biosystems DNA editing and assembly software and sequence comparisons were obtained using the Microseq software.

The analyzed sequence showed a 0% mismatch (or 100% match) over the analyzed >500 bp to B. subtilis subtilis.

Example 3

Sensory Evaluation 0.15 ml of the 10 fold of example 1a and 1 ml of the single fold vanilla extracts of example 1b and as control commercially available 10 fold and single fold extract from traditionally cured vanilla beans (subjected to a standard curing process over several months) were added to 100 ml of sweetened milk (5% sucrose) and compared in a sensory evaluation by trained panelists.

Trained panelists compared the samples and the control.

All panelists noted a very clean well-balanced vanilla profile without off-notes and a very strong vanillin note in sample 1a, which was much stronger than in the standard 10 fold vanilla extract. The impact of vanillin was lower in sample 1b but the panelists found the sample sweeter.

Panelists found all samples had a well-developed well-balanced vanilla aroma.

Example 4

Consistent Flavor Profile 5 batches were produced as described in example 1a, with the same amount and concentration of B. subtilis, but with slight variations in incubation temperature (40° C. to 65° C.) and length, or washing steps (heat or rinsing with 70% alcohol).

The resulting vanilla extracts were tasted by 5 trained panelists.

Samples are evaluated based on a 1-10 preference scale, with a control reference of high quality bourbon vanilla bean extract (traditionally cured) with a vanillin concentration of at least 1.5%, good vanilla flavor and no detectable off-notes (8).

Vanilla extracts from commercial sources either traditionally cured can range from 1 (least preferred, no fullbodied vanilla flavor, unbalanced flavor profile, presence of green, beany, fatty acid, moldy, or smoky notes) to 10 (perfectly balanced vanilla flavor with low concentration of phenolic/guaiacol off-notes, and no presence of any other off-notes). A good quality commercially available vanilla extract usually ranges from 5 to 8. Vanilla extracts formed not through traditional curing but through various alternative processes perform significantly lower and need to be mixed with better quality extracts for commercial sales. Even though the batches varied slightly in temperature etc., all 5 batches fell within a narrow range at the higher end of the 1-10 scale (8-10), demonstrating a consistently high vanilla flavor quality.

Example 5

Effect of Lack of Drying/Temperature and B. Subtilis Concentration

A vanilla bean extract was prepared as described in example 1a. It was compared to an extract formed from non-dried beans naturally cured at 20 to 25 C (ambient temperature) on the vine and no added B. subtilis apart from the naturally occurring bacterial population. The sensory evaluation was performed as described in example 4.

The extract of example 1 scored at 9, the naturally cured beans at 1 (even though they had a high vanillin concentration of 3%).

Example 6

Conversion of Vanilla Flavor Precursor Compounds to Vanilla Flavour by B. Subtilis Gluco-vanillin was added to a culture of B. subtilis subtilis strain NRRL B-50118, isolated from vanilla beans and deposited Mar. 20, 2008 with the ARS Patent Culture Collection. The B. subtilis culture was prepared in nutrient broth (Bacto™ nutrient broth dehydrated for cultivation of non fastidious microorganisms, Difco, Laboratories Detroit, Mich., USA, 8 g/l of distilled water) and grown to an OD600 of 0.6-2.0 prior to the addition of gluco-vanillin.

After addition of glucovanillin, the B. subtilis culture was incubated for 120 h at a temperature of 37° C.

Samples were taken as indicated in the table below to detect vanillin and various intermediates of the conversion of glucovanillin to vanillin.

The results are indicated in the table below.

| Compound | 1 h [ppm] | 2 h [ppm] | 5 h [ppm] | 7 h [ppm] | 9 h [ppm] | 26 h [ppm] | 48 h [ppm] | 120 h [ppm] |
|---|---|---|---|---|---|---|---|---|
| gluco-vanillin | 3300 | 3200 | 3000 | 2900 | 1300 | 100 | 0 | 0 |
| guaiacol | 1.35 | 1.90 | 6.48 | 14.3 | 306 | 139.6 | 207 | 295 |
| benzoic acid | 0 | 0 | 0 | 0 | 20.2 | 20.9 | 27.3 | 19.0 |
| 4-methyl-guaiacol | 0.23 | 0.10 | 0.07 | 0.07 | 2.97 | 10.2 | 13.3 | 25.0 |
| vanillylalcohol | 55.3 | 18.8 | 20.2 | 35.4 | 31.3 | 107.2 | 192.9 | 144.6 |
| vanillic acid | 0 | 142 | 141 | 163 | 200 | 200 | 300 | 800 |
| vanillin | 50 | 80 | 200 | 210 | 40 | 80 | 70 | 30 |

Gluco-vanillin was completely digested to vanillin within 26 hrs. The concentration of vanillin increased to 210 ppm at 7 hours, and then decreased again. The concentration of 4-methylguaiacol, benzoic acid, vanillylalcohol, and vanillic acid increase relatively constantly over the measuring time, except for some minor fluctuations, especially for the lower or higher concentrations (for example guaiacol and vanillyl alcohol).

In a second experiment, the same *B. subtilis* strain was incubated as described above with the glucoside of p-glucobenzaldehyde.

Phenol can be formed from p-glucobenzaldehyde (p-GBA) enzymatically, for example by beta-glucosidase which forms p-hydroxybenzaldehyde (p-HBA), and then p-hydroxybenzaldehydedehydrogenase which forms p-hydroxybenzoic acid (p-HBAc), and in the last step p-hydroxybenzoatedecarboxylase which forms phenol.

The fermentation broth was analyzed in regular intervals by High Performance Liquid Chromatography/HPLC (non-volatiles) or Gas Chromatography/GC (volatiles, phenol) as indicated in the table below.

The results are indicated in the table below.

| | 1 d [ppm] | 6 d [ppm] | 9 d [ppm] | 14 d [ppm] | 19 d [ppm] |
|---|---|---|---|---|---|
| p-GBA (HPLC) | 0 | (0.5) | 0 | 0 | 0 |
| p-HBA (HPLC) | 239 | 204 | 176 | 46 | 2 |
| p-HBAc (HPLC) | 27 | 83 | 115 | 244 | 285 |
| Phenol (GC) | 0.59 | 8.58 | 8.35 | 23.15 | 33.9 |

The results show that over the time the concentration of phenol increases, while p-glucobenzaldehyde decreases rapidly to 0 within 24 hours (except for one measuring point). At the same time the intermediates (p-hydroxybenzaldehyde and p-hydroxybenzoic acid) have formed, and with continued formation of phenol, p-HBA decreases again. The measurements of phenol analyzed by GC are not directly comparable but show that phenol is formed and increases over time, whereas its precursor and intermediates decrease.

While the processes and products have been described above in connection with certain illustrative embodiments, it is to be understood that other similar embodiments may be used or modifications and additions may be made to the described embodiments for performing the same function(s). Further, all embodiments disclosed are not necessarily in the alternative, as various embodiments may be combined to provide the desired characteristics. Variations can be made by one having ordinary skill in the art without departing from the spirit and scope of the disclosure. Therefore, the processes and products should not be limited to any single embodiment, but rather construed in breadth and scope in accordance with the recitation of the attached claims.

The invention claimed is:

1. A process of fermenting vanilla beans comprising the step of incubating uncured vanilla beans with *Bacillus subtilis* in isolated form, wherein the incubation with *B. subtilis* lasts for about 24 hours to about 120 hours, and wherein before incubation with *B. subtilis*, the uncured vanilla beans are dried until a moisture concentration of less than 10% is reached, and then treated with a water containing composition comprising *Bacillus subtilis*.

2. The process of claim 1 wherein the incubation with *B. subtilis* is performed at a temperature from about 40° C. to about 65° C.

3. The process of claim 1, wherein before being dried, the uncured vanilla beans are washed.

4. The process of claim 1, wherein after the incubation with *B. subtilis*, one or more enzymes comprising a beta-glucosidase enzyme are added.

5. The process of claim 1 wherein a solvent is added to the resulting product to form a vanilla extract.

6. The process of claim 1 wherein the incubation with *B. subtilis* is performed in a vessel selected from the group consisting of: a sweating tank wherein the vanilla beans are stationary, and a stirred tank.

7. The process of claim 6 wherein the incubation with *B. subtilis* is performed in a closed system of a sweating tank wherein the vanilla beans are stationary and wherein the exudate from the vanilla beans is being recycled.

8. The process of claim 1 wherein the incubation with *B. subtilis* is performed in an open system.

9. The process of claim 1, wherein *B. subtilis* is selected from the group consisting of *B. subtilis subtilis*, a wildtype *B. subtilis* strain isolated from vanilla beans, and *B. subtilis subtilis* strain NRRL B-50118.

10. A process according to claim 1, wherein the *B. subtilis* is provided in isolated form.

11. A process according to claim 1, wherein the *B. subtilis* used in the fermentation step is provided from a stock culture or as a pre-culture.

12. The process according to claim 3, wherein the beans are washed in a temperature of between 20-85° C.

13. The process according to claim 3, wherein the beans are washed for between 1-10 minutes.

* * * * *